US006579866B2

(12) United States Patent
McCleary

(10) Patent No.: US 6,579,866 B2
(45) Date of Patent: Jun. 17, 2003

(54) COMPOSITION AND METHOD FOR MODULATING NUTRIENT PARTITIONING

(76) Inventor: Larry McCleary, 1795 Foothills Dr. South, Golden, CO (US) 80401

( * ) Notice: Subject to any disclaimer, the term of this patent is extended or adjusted under 35 U.S.C. 154(b) by 204 days.

(21) Appl. No.: 09/749,584

(22) Filed: Dec. 28, 2000

(65) Prior Publication Data

US 2002/0132219 A1 Sep. 19, 2002

(51) Int. Cl.[7] .............................................. A61K 3/555
(52) U.S. Cl. ...................... 514/188; 514/556; 514/505; 514/549; 424/665
(58) Field of Search ................. 424/94.1, 183, 424/523, 655; 930/240; 514/188, 505, 556, 506, 547, 557, 392, 387, 549

(56) References Cited

U.S. PATENT DOCUMENTS

| | | | |
|---|---|---|---|
| 4,599,232 A | | 7/1986 | Bertelli ....................... 424/94.1 |
| 5,626,849 A | * | 5/1997 | Hastings et al. ............ 514/188 |
| 5,744,161 A | * | 4/1998 | Majeed et al. |
| 5,895,652 A | | 4/1999 | Giampapa .............. 424/195.17 |
| 5,914,326 A | * | 6/1999 | McCarty et al. ............ 514/188 |
| 5,973,004 A | | 10/1999 | Howard ....................... 514/561 |
| 6,020,378 A | | 2/2000 | Cook et al. ................. 514/560 |
| 6,048,846 A | | 4/2000 | Cochran ..................... 514/168 |
| 6,277,396 B1 | * | 8/2001 | Dente ......................... 424/439 |
| 6,277,842 B1 | * | 8/2001 | Carthron .................... 514/188 |

FOREIGN PATENT DOCUMENTS

| | | |
|---|---|---|
| DE | 4304394 | 9/1993 |
| EP | 0779033 | 6/1997 |
| WO | WO 8901740 | 3/1989 |

* cited by examiner

*Primary Examiner*—Jean C. Witz
(74) *Attorney, Agent, or Firm*—Patton Boggs LLP

(57) ABSTRACT

A nutritional supplement composition for modulating nutrient partitioning in a human so as to increase oxidation of fat and promote increased storage of glycogen is composed of hydroxycitric acid, carnitine, biotin, a gluconeogenic substrate, and, optionally, one or more of chromium, conjugated linoleic acid, coenzyme Q10, eicosapentaenoic acid, pyridoxine, alpha-lipoic acid, magnesium, and gymnema sylvestre. A method for modulating nutrient partitioning in a human involves orally or parenterally administering the aforementioned composition to the human, preferably on a daily basis, for a therapeutically effective period of time. Preferably, the method further involves having the human follow a specific dietary regimen wherein the glycemic index is less than 60 and the daily calorie consumption from carbohydrates is less than about 50% and the daily calorie consumption from protein is at least about 20%. Optionally, the method further involves an exercise program, a stress reduction program and/or a blood donation program.

24 Claims, No Drawings

COMPOSITION AND METHOD FOR MODULATING NUTRIENT PARTITIONING

BACKGROUND OF THE INVENTION

This invention relates to compositions and methods for modulating nutrient partitioning. More particularly, the present invention provides a composition and a method for modulating nutrient partitioning in humans so as to normalize nutrient pathways which play a key role in numerous metabolic disorders, the composition and method being designed to prevent, delay or reverse such disorders.

Disorders of nutrient partitioning leading to biochemical signaling abnormalities form the basis for a group of metabolic disorders. These include but are not limited to insulin resistance, hyperinsulinemia, Syndrome X, hypertriglyceridemia and/or low HDL syndrome, high RQ (respiratory quotient) syndrome, obesity, chronic fatigue syndrome, small dense LDL syndrome, recidivism from weight loss, glucolipoxia, premature aging, memory loss, endothelial dysfunction, vascular disease, hypertension, postprandial hyperlipidemia, certain types of cancer, metabolic inflexibility and others. The basic abnormality is similar in each circumstance but manifests clinically in different ways depending upon the organ involved, the individual's genetic makeup, age, sex and other factors.

The two major macronutrient fuels are fat and carbohydrate (which is stored in the body as glycogen). In the body, fat and carbohydrate are combined in certain proportions to generate the fuel mix the body burns at any point in time. If the fuel mix contains more carbohydrate, it contains relatively less fat and vice versa. Because there is minimal metabolic transformation between carbohydrate and fat, if more fat is being burned, then less is being stored and vice versa. The same holds true for carbohydrate, i.e., if more carbohydrate is being burned, then less is being stored and vice versa.

The relative ratio of fat and carbohydrate contributing to the fat/carbohydrate fuel mix is referred to as the "respiratory quotient" (RQ). RQ is approximately 1 when only carbohydrate is being burned and is about 0.8 when fat is the sole component being oxidized. A mixture of fuels is assigned a number between approximately 0.8 and 1.0. The nutrient partitioning abnormality most frequently encountered as manifested by an elevated RQ indicates excessive fat storage associated with excessive combustion of carbohydrate. This condition predisposes to increased intracellular lipid stores in numerous organ systems as well as the entire body. The most affected organs are the liver, pancreas, adipose tissue and skeletal muscle. Also involved is the hypothalamic-pituitary-adrenal axis as well as the vascular wall. When lipid stores accumulate in these organs, they produce alterations in intracellular signaling systems including insulin and protein kinase C (PKC) signaling pathways leading to skeletal muscle insulin resistance, excessive basal insulin secretion by the pancreas associated with a decrement in glucose-induced insulin release, an impairment of insulin action at the level of the liver manifested by decreased sensitivity of insulin suppression of hepatic glucose output, expansion of (visceral) fat stores, excessive cortisol secretion and endothelial dysfunction associated with altered nitric oxide physiology. The defects primarily involving insulin signaling pathways act as predisposing factors which increase tissue glycation and oxidative stress. This constellation of abnormalities combines in various ways to form the basis for the metabolic diseases mentioned above.

For various reasons, approximately 30% to 50% of the population of westernized societies manifest overtly abnormal fuel homeostasis. As a result, affected individuals have a predisposition to accumulate intracellular lipid in various tissues and organs, which alters the intracellular metabolic milieu and induces alterations in various strategic signal transduction systems, as discussed above. Such alterations induce different metabolic and physiologic alterations among individuals. In one person, obesity might result, while another may develop hypertension, non-insulin dependent diabetes mellitis (NIDDM), dyslipidemia or vascular disease depending upon specific genetic interactions. Other people might evolve symptoms based upon oxidative stress and enhanced tissue glycation, causing external signs of premature aging or memory loss. In some circumstances, the primary abnormality may be only augmented IGF effects, leading to the development of prostatic hypertrophy or frank prostate cancer in an individual.

It is desirable, therefore, to provide a means for modulating (i.e., altering or normalizing) aberrant pathways of nutrient partitioning which play a key role in numerous metabolic disorders. More particularly, it is desirable to provide a means for modulating aberrant pathways of nutrient partitioning so as to avoid excessive fat storage and excessive carbohydrate oxidation. Specifically, it is desirable to provide a means for modulating aberrant pathways of nutrient partitioning so as to promote oxidation of fat and storage of carbohydrate (glycogen).

Compositions and methods designed to reduce fat levels or otherwise improve metabolism in the body are known in the art.

A weight loss composition designed to burn and reduce synthesis of fats is disclosed, e.g., in U.S. Pat. No. 5,626,849 to Hastings et al. The composition taught in Hastings et al. contains chromium, L-carnitine, gamma-linoleic acid, (−) hydroxycitric acid, choline, inositol, antioxidants and herbs. The preferred antioxidants are said to be Coenzyme Q10.

U.S. Pat. No. 6,020,378 to Cook et al. discloses a method for selectively altering body fat levels in animals involving administering to the animal a combination of conjugated linoleic acid isomers in a ratio selected to retain a desirable benefit attributable to one isomer while counteracting an undesirable effect of the same isomer.

European patent application no. EP0779033 discloses an edible fat spread which is said to contribute to an improved blood lipid profile. The spread contains triglyceride fat the fatty acid residues of which includes conjugated linoleic acid (CIA) residues.

U.S. Pat. No. 5,895,652 to Giampapa discloses a method and composition which are said to supply key elements necessary for proper metabolization and function of the human body, wherein the composition includes vitamins, minerals, plant extracts, aminos, neurochemical precursors, enzymes and pH regulating agents.

U.S. Pat. No. 4,599,232 to Bertelli discloses a pharmaceutical composition for treatment of tissue energetic and metabolic disorders, wherein the composition contains carnitine or acetylcarnitine and coenzyme Q10 in ratios from 100:1 to 2:1, together with pharmaceutically acceptable excipients.

U.S. Pat. No. 5,973,004 to Howard discloses a composition for oral or parenteral administration to animals for prevention or treatment of syndromes or diseases arising from dysfunctional energy metabolism. The Howard composition includes a combination of L-carnitine and acetyl-L-carnitine, preferably with pantothenic acid or ubiquinone.

U.S. Pat. No. 6,048,846 to Cochran discloses a composition which is said to fight disease and restore the conditions of the body on a cellular level, wherein the composition contains specific and calculated quantities of hormones, amino acids, amino sugars, coenzymes, enzymes and mineral ions.

German patent no. DE 4304394A1 (abstract) discloses a composition for nourishing oncological patients, composed of fats and optionally proteins and/or carbohydrates, wherein the fat contains oleic acid, linoleic acid, alpha lipoic acid, eicosapentanoic acid and docosahexanoic acid.

WO 89/01740 discloses a composition intended for diet fortification to increase the efficiency of muscle work wherein the composition includes coenzyme Q10 as an essential component, along with nutrients, salts, vitamins, trace substances, flavorings, aromatics, etc.

None of the foregoing references is specifically concerned with the issue of altering the nutrient partitioning in the body so as to increase oxidation of fat and storage of carbohydrate (in the form of glycogen).

Accordingly, the primary object of this invention is to provide a composition and method for modulating nutrient partitioning in the body so as to increase oxidation of fat and storage of glycogen.

This object is achieved in the present invention.

SUMMARY OF THE INVENTION

The present invention is directed to a method and a nutritional supplement composition for modulating nutrient partitioning in the body so as to increase oxidation of fat and promote increased storage of glycogen. The composition of this invention is composed of effective amounts of hydroxycitric acid (HCA), carnitine, biotin, and a gluconeogenic substrate. Optionally, the composition contains one or more of the following: chromium, conjugated linoleic acid (CLA), coenzyme Q10, eicosapentaenoic acid (EPA), pyridoxine, alpha-lipoic acid, magnesium, and gymnema sylvestre. The method of this invention involves orally administering to a human on a daily basis for a therapeutically effective period of time the composition of this invention In a preferred embodiment, the method of this invention further involves following on a daily basis a dietary regimen wherein the carbohydrate content is less than about 50% of the total daily caloric intake, the glycemic index is less than about 60, and the protein content is at least about 20% of the total caloric intake. In a particularly preferred embodiment, the dietary regimen involves a multiple of small meals per day, preferably 4 to 6 meals per day. Optionally, the method of this invention further involves an exercise program and/or stress reduction program and/or blood donation program.

By modulating nutrient partitioning so as to increase oxidation of fat and promote increased storage of glycogen, the present invention promotes the normalization of macronutrient fuel partitioning pathways which contribute to or form the basis for a group of metabolic diseases. The composition and method of this invention modulate processes at the very core of each of these diseases. In so doing, the invention induces changes which are beneficially amplified at each metabolic branch point in ways designed to normalize the fundamental metabolic defect in each affected individual.

The invention also promotes accretion of lean body mass and can augment exercise performance.

With the method and composition of this invention, diminished fat synthesis and storage are accomplished coincidentally, resulting in a fall in the intracellular fat content of the liver, pancreas, and skeletal muscle as well as a fall in visceral fat and total body fat stores accompanied by a decrease in individual fat cell volume. These effects improve insulin sensitivity, decrease serum insulin levels, decrease RQ, decrease fasting serum TG and VLDL levels, decrease postprandial hyperlipidemia, downregulate cortisol production and activity, improve endothelial function, decrease the concentration of small dense LDL particles, and elevates existing low levels of HDL.

In addition, unlike other weight loss programs which reduce metabolic rate, temperature, and energy and increases hunger sensations, the present invention increases metabolic rate, temperature, and energy and decreases appetite.

Thus, with the method and composition of this invention, energy levels are elevated, appetite is suppressed, lean body mass is increased, thermogenesis is upregulated, and tendency to regain weight is diminished. These effects collectively act to prevent, reverse, or lessen the adverse metabolic diseases described herein.

DETAILED DESCRIPTION OF THE INVENTION

As stated above, the present invention provides a method and composition for modulating nutrient partitioning so as to increase oxidation of fat and increase storage of glycogen. As used herein, the term "modulating" with respect to the effect of the composition and method of this invention on nutrient partitioning means that the composition and method have a beneficial effect on the ratio of fat and carbohydrate in the fuel mix discussed previously herein. More specifically, the term "modulating" means that the composition and method of this invention alter or normalize nutrient partitioning so as to increase fat oxidation and glycogen storage, which in turn reduces the RQ value (i.e., more fat and less carbohydrate is burned).

The method of the invention involves the daily administration of an effective amount of the composition preferably in conjunction with a specific dietary plan in a synergistic format. The method may include an exercise program and/or stress reduction program and/or blood donation program.

The composition of this invention is composed of effective amounts of: HCA, carnitine, biotin, and a gluconeogenic substrate preferably selected from one or more of the following: aspartate, lactate, glycerol, and any gluconeogenic amino acid or its alpha-keto analogue. The gluconeogenic amino acid is preferably alanine, arginine, asparagine, cystine, glutamine, glycine, histidine, hydroxyproline, methionine, proline, serine, threonine and valine.

Preferably, the composition of this invention further contains one or more of the following: chromium, CLA, coenzyme Q10, EPA (either alone or as part of fish oil), pyridoxine, alpha lipoic acid, magnesium, and gymnema sylvestre.

HCA and carnitine promote hepatic fatty acid oxidation by activating carnitine palmitoyl transferase (CPT), the rate-limiting enzyme in the fatty acid oxidation process.

EPA (either alone or as part of fish oil) inhibits the enzymes citrate lyase (CL) and acetyl CoA carboxylase (ACC), thus inhibiting the production of malonyl CoA—an allosteric inhibitor of CPT. EPA/fish oil thus acts to disinhibit fatty acid oxidation.

As one of its metabolic effects, CLA promotes fat-to-lean partitioning changes via the activation of CPT.

Thus, HCA, carnitine, EPA, and CLA promote or disinhibit hepatic fatty acid oxidation.

Hepatic fat oxidation produces reducing equivalents, ATP, and acetyl CoA which drive hepatic gluconeogenesis. The elevated acetyl CoA levels activate the liver enzyme pyruvate carboxylase (PC) and high ATP levels inhibit pyruvate dehydrogenase (PDH). These effects synergistically accelerate hepatic gluconeogenesis while simultaneously inhibiting fat synthesis. The reducing equivalents generated by disinhibited fatty acid oxidation are consumed in the reductive synthetic processes of gluconeogenesis.

Hepatic gluconeogenesis acts via the indirect route to expand liver glycogen stores and provides a slow continuous time release source of glucose from the liver. Both of these have the physiologic effect of profoundly suppressing appetite and increasing energy. These effects are enhanced by the consumption of appropriate amounts of low glycemic index carbohydrates whose glucose content is absorbed slowly over a prolonged time interval, thus acting as a sustained release glucose source emanating from the gut.

It has also been shown that hepatic triglyceride (TG) synthesis as well as very low density lipoprotein (VLDL) secretion are diminished coincidentally with increasing hepatic fatty acid (A) oxidation.

Coenzyme Q10 facilitates respiratory chain function and hence augments the process of reverse electron transport. This process plays a key role in the thermogenic effect produced by accelerated fatty acid oxidation.

Biotin induces the up regulation of the enzyme glucokinase (GK) in the pancreas and enhances the process of glucose-induced insulin secretion. In addition, biotin counteracts the effect HCA has on the pancreas. HCA tends to inhibit glucose-induced insulin secretion, while biotin facilitates it by activating GK. Together, HCA and biotin maximize pancreatic fuel homeostasis.

Pyridoxine supplementation augments physiological levels of pyridoxal phosphate. This compound interacts with glucocorticoid receptors to down-regulate their activity and hence to diminish glucocorticoid effects throughout the body. This action tends to decrease visceral fat accumulation as well as promote insulin sensitivity. Improved insulin sensitivity contributes to insulin-induced appetite suppression. In addition, a direct consequence of improved insulin sensitivity is a decrease in the activity of insulin like growth factor (IGF), a potent cancer inductive agent.

Chromium improves insulin sensitivity in the central nervous system and skeletal muscle. The former contributes to insulin-induced appetite suppression at the level of the hypothalamus while the latter improves insulin-induced glucose disposal into skeletal muscle. In the present invention, chromium can be added in the form of a non-toxic salt, such as, e.g., chromium diglycinate, chromium arginate, chromium picolinate, and the like.

CLA, alpha lipoic acid, gymnema sylvestre, coenzyme Q10 and magnesium each have insulin sensitizing effects. In this invention, magnesium can be added in the form of a non-toxic salt.

With respect to the amounts of the individual components of the composition of this invention, the term "effective amount" means that amount of the component which, when used in combination with the other components in the composition, will provide the composition with the capability of modulating nutrient partitioning so as to increase oxidation of fat and promote increased storage of glycogen.

Preferably, the composition contains an HCA:carnitine weight ratio of from about 1:10 to about 100:1, an HCA biotin weight ratio of from about 50:1 to about 2500:1, and an HCA:gluconeogenic substrate weight ratio of from about 5:1 to about 1:60.

The composition of this invention preferably includes a pharmaceutically acceptable carrier. As used herein, the term "pharmaceutically acceptable carrier" is meant to include one or more pharmaceutically suitable, inactive excipients, carriers, diluents, adjuvants, and lubricants. Non-limiting examples of inactive excipients, carriers, diluents, lubricants, and adjuvants which can be used in the composition of the present invention include: cellulose, substituted cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicium dioxide, food glaze, talc, croscarmellose sodium, povidone, water and gelatin. Additional inactive excipients, carriers, diluents, lubricants and adjuvants which may be used with the active-ingredient composition of this invention are disclosed in the Handbook of Food Additives (CRC Press), which is incorporated by reference herein in relevant part.

The pharmaceutically acceptable carrier can be present in any conventional amount used in an orally administered composition.

Set forth in Table I below is a preferred embodiment of the orally administered composition (excluding inactive ingredients) of this invention. Table II sets forth a more preferred embodiment of the composition. The amounts recited in Tables I and II represent the preferred daily dosage of the ingredients listed.

TABLE I

Orally Administered Composition
Preferred Daily Dosage

| | |
|---|---|
| Gluconeogenic Substrate | 1–75 grams |
| HCA | 0.2–8 grams |
| Carnitine | 10 milligrams–10 grams |
| Biotin | 1–25 milligrams |
| Chromium | 100 micrograms–2 milligrams |
| CLA | 50 milligrams–20 grams |
| EPA (alone or as a component of fish body oil) | 10 milligrams–10 grams |
| Coenzyme Q10 | 5–500 milligrams |
| Alpha Lipoic Acid | 25–2000 milligrams |
| Magnesium | 200–1600 milligrams |
| Pyridoxine | 25–400 milligrams |
| Gymnemic Acid (from gymnemic sylvestre) | 20–2000 milligrams |

TABLE II

Orally Administered Composition
More Preferred Daily Dosage

| | |
|---|---|
| Gluconeogenic Substrate | 1–30 grams |
| HCA | 0.5–5 grams |
| Carnitine | 50–5000 milligrams |
| Biotin | 2–10 milligrams |
| Chromium | 400–1000 micrograms |
| CLA | 1–10 grams |
| EPA (alone or as a component of fish body oil) | 50–5000 milligrams |
| Coenzyme Q10 | 10–400 milligrams |
| Alpha Lipoic Acid | 50–800 milligrams |
| Magnesium | 400–1200 milligrams |
| Pyridoxine | 100–300 milligrams |
| Gymnemic Acid | 75–500 milligrams |

The composition presented in the Tables above is preferably in the form of an orally administered composition, e.g., powder, chewable wafer, tablet, regular or compressed capsule, etc., wherein the amounts listed are divided into two portions which in combination constitute a single "serving" or "unit dose" of the composition. Each serving is preferably with 8 ounces of water.

The method of this invention involves the steps of administering to a human on a daily basis for a therapeutically effective period of time an effective amount of the composition of this invention. The composition is administered orally or parenterally, preferably orally.

As used herein with respect to the amount of the composition used in the method of this invention, the term "effective amount" means an amount sufficient to modulate nutrient partitioning in the body so as to increase oxidation of fat and increase storage of glycogen. Preferably, the active-ingredient composition (not including inactive ingredients) of this invention is administered in a per serving (e.g., daily) dosage of at least about 1 gram, more preferably from about 1 gram to about 200 grams, most preferably from about 4 grams to about 20 grams. When inactive ingredients are present in the composition, the inactive ingredients of the composition can be present in any conventional amount used in orally or parenterally administered compositions.

The term "therapeutically effective period of time" with respect to the administration of the composition in the method of this invention means that period of time sufficient to modulate nutrient partitioning in the human. Preferably, the composition of this invention is administered on a daily basis for a period of at least three weeks, more preferably at least six weeks.

As stated above, oral administration is accomplished by ingesting the composition, preferably with water. The orally administered composition of this invention can be in any conventional form including, e.g., capsules (regular or compressed), tablets, chewable wafers, elixirs, powders, granules, suspensions in water or non-aqueous media, sachets, etc. Powder, tablet, and chewable wafer forms are most preferred.

Alternatively, the composition can be administered parenterally.

As stated previously herein, the method of the invention preferably involves the administration, preferably daily oral administration, of the above-described composition in conjunction with a specific dietary plan in a synergistic format. The dietary plan preferably involves multiple small meals, each reflecting the overall macronutrient composition of the diet. Carbohydrate content is low as is the glycemic index. Protein content is high. In the dietary regimen followed in the present invention, the glycemic index is preferably less than 60, more preferably less than 45; the carbohydrate content will constitute less than 50%, more preferably 0–50%, most preferably about 7–40% of the calories consumed on a daily basis; and the protein intake constitutes preferably at least 20%, more preferably about 20–40%, most preferably about 25–35% of total daily caloric intake. The number of meals is preferably 2, more preferably 4 to 6, per day. Adequate fluid intake is recommended to insure excellent hydration.

As stated above, the composition of this invention is preferably administered on a daily basis. However, if desired, the composition can be administered on a non-daily basis, e.g., every other day. The frequency of administration will depend on how fast the individual wishes to lose weight. The more frequent the composition is administered, the faster the weight loss. Thus, daily administration of the composition will result in faster weight loss than non-daily administration.

Low glycemic index, low carbohydrate, high protein diets have the physiologic effect of inducing low serum insulin (I) levels and low serum insulin/glucagon (I/G) ratios. Both of these parameters act to disinhibit hepatic fatty acid oxidation by decreasing malonyl CoA levels and desensitizing CPT to inhibition by malonyl CoA. On the other hand, if a high carbohydrate diet (greater than 50% carbohydrates) is consumed, average daily insulin levels and the I/G ratio are increased, thereby adversely impacting CPT activity and acting to inhibit fat oxidation.

The method of this invention preferably further includes an exercise program. Preferably, the exercise program will be followed at least 2 days a week and more preferably 3 to 5 days per week. The exercise program should preferably include components of aerobic and resistance training as tolerated by the individual in need thereof.

The exercise program augments fatty acid oxidation during the period of active exercise as well as inducing a fall in RQ post exercise. Insulin sensitivity is increased after each bout of exercise as well as with exercise training. Exercise programs produce changes parallel to those described herein which augment insulin sensitivity, facilitate energy expenditure and reduce RQ for an extended period of time post exercise.

The invention may further include a stress reduction program designed to diminish glucocorticoid activity. By downgrading glucocorticoid activity, the stress reduction program acts to improve insulin sensitivity and decrease visceral obesity. Utilizing similar mechanisms, pyridoxine augments both these actions. The stress reduction program may involve any activity that lowers glucocorticoid levels. Non-limiting examples of such activities include relaxation, getting a massage, acupuncture, psychotherapy, meditation, taking a sedative, and the like.

The method of the present invention may also include a blood donation program. Blood may be given about every 56 days. This produces a fall in both serum ferritin levels and iron stores within the body which together decrease oxidative stress and improve insulin sensitivity. The amount of blood donated will depend on the individual's serum ferritin levels. Generally, the frequency and amount of blood donated should be such as to provide a serum ferritin level of from about 25 to about 50 nanograms/milliliter of serum.

The method of this invention results in marked increases in fat oxidation and glycogen storage while simultaneously minimizing fat synthesis and storage.

Without being bound by any particular overall mechanistic explanation of the invention, the effects of the present invention upon hormone levels and ratios (i.e., low I level, low I/G ratio) facilitate the release of fatty acids for presentation at the hepatocyte mitochondrial membrane. At this locus resides the enzyme CPT. As stated previously herein, CPT is the rate-limiting enzyme in the oxidation of activated long chain fatty acids. Carnitine represents the essential cofactor for CPT and is generally in the subsaturating range in the liver. Exogenous supplementation of carnitine augments CPT activity. Low I levels and a low I/G ratio tend to cause carnitine uptake and concentration in hepatocytes, which in turn acts to increase CPT activity in the liver.

Malonyl CoA, a potent inhibitor of CPT, is a cytosolic metabolite derived from citrate. The cytosolic enzymes CL and ACC are involved in metabolizing cytosolic citrate to acetyl CoA and then on to malonyl CoA, respectively. HCA is a potent competitive inhibitor of CL, thus acting to decrease malonyl CoA levels. EPA/fish oil decreases the activity of both CL and ACC and make CPT less sensitive to the inhibitory effects of malonyl CoA. The effect of the low I level and low I/G ratio resulting from the dietary plan additionally diminishes the activity of CL and ACC and have a similar desensitizing effect on CPT to the inhibitory action of malonyl CoA. CLA also serves to activate CPT. The action derived from the combined effect of these mechanisms profoundly disinhibits fatty acid oxidation.

Hepatic oxidation of fatty acids to acetyl CoA proceeds independently of the rate of generation of ADP by the liver. This induces the production of mitochondrial acetyl CoA and ATP at high rates. Reducing equivalents in the form of NADH and FADH$_2$ are also abundantly generated. These effects combine to upregulate reverse electron transport—a highly thermogenic process. In addition, the enzyme PC is activated by the production of high levels of acetyl CoA. At the same time, the enzyme PDH is inhibited by the high ATP levels. Together, these actions channel substrate into the gluconeogenic pathways and away from fat synthetic pathways. The reducing equivalents generated by activation of the fatty acid oxidation process also drive gluconeogenesis. The gluconeogenic process is also thermogenic and is coupled with replenishment of hepatic glycogen stores via the indirect pathway as well as enhanced hepatic glucose output—a process that provides a continuous slow time release source of serum glucose. The gluconeogenesis substrate used in the invention acts as substrate for the gluconeogenic pathway, further acting to facilitate gluconeogenesis. Because the gluconeogenesis substrate is provided exogenously, it tends to spare muscle protein breakdown, thus acting in an anticatabolic fashion and promoting expansion of lean tissue mass. The net effect of this combination of metabolic actions is to profoundly suppress appetite while increasing energy levels, and at the same time oxidizing fat at high rates in a thermogenic fashion. These combine to decrease energy intake while enhancing energy expenditure. This causes a significant depression of RQ as a reflection of the profound alteration in fuel homeostasis and nutrient partitioning which are induced. This lowers the risk of recurrent weight gain following prior weight loss.

What is claimed is:

1. In an orally or parenterally administered composition for modulating nutrient partitioning in a human so as to increase oxidation of fat and increase storage of glycogen comprising
    an effective amount of hydroxycitric acid;
    an effective amount of carnitine;
    an effective amount of biotin; and
    an effective amount of one or more gluconeogenic substrates selected from the group consisting of aspartate, lactate, glycerol, and a gluconeogenic amino acid or alphaketo analogue thereof;
    the improvement comprising the addition of an effective amount of eicosapentanoic acid.

2. A composition according to claim 1, wherein the composition comprises: a weight ratio of the hydroxycitric acid to the carnitine of from about 1:10 to about 100:1; a weight ratio of the hydroxycitric acid to the gluconeogenic substrate of from about 5:1 to about 1:60; and a weight ratio of the hydroxycitric acid to the biotin of from about 50:1 to about 2500:1.

3. A composition according to claim 1, wherein the gluconeogenic amino acid is selected from the group consisting of: alanine, arginine, asparagine, cystine, glutamine, glycine, histidine, hydroxyproline, methionine, proline, serine, threonine, and valine.

4. A composition according to claim 1, wherein the composition further comprises an effective amount of at least one nutritional supplement.

5. A composition according to claim 4, wherein the nutritional supplement is selected from the group consisting of: chromium, conjugated linoleic acid, coenzyme Q10, eicosapentaenoic acid, pyridoxine, alpha-lipoic acid, magnesium, and gymnema sylvestre.

6. A composition according to claim 5, comprising: from about 0.2 grams to about 8 grams of hydroxycitric acid, from about 10 milligrams to about 10 grams of carnitine, from about 1 gram to about 75 grams of the gluconeogenic substrate; from about 1 milligram to about 25 milligrams of biotin, from about 100 micrograms to about 2 milligrams of chromium, from about 5 milligrams to about 500 milligrams of coenzyme Q10, from about 50 milligrams to about 20 grams of conjugated linoleic acid, from about 10 milligrams to about 10 grams of eicosapentaenoic acid, from about 25 milligrams to about 400 milligrams of pyridoxine, from about 25 milligrams to about 2000 milligrams of alpha lipoic acid, from about 200 milligrams to about 1600 milligrams of magnesium, and from about 20 milligrams to about 2000 milligrams of gymnemic acid.

7. A composition according to claim 5, comprising: from about 0.5 grams to about 5 grams of hydroxycitric acid, from about 50 milligrams to about 5 grams of carnitine, from about 1 gram to about 30 grams of the gluconeogenic substrate; from about 2 milligrams to about 10 milligrams of biotin, from about 400 micrograms to about 1000 micrograms of chromium, from about 20 milligrams to about 300 milligrams of coenzyme Q10, from about 1 gram to about 10 grams of conjugated linoleic acid, from about 50 milligrams to about 5000 milligrams of eicosapentaenoic acid, from about 100 milligrams to about 300 milligrams of pyridoxine, from about 50 milligrams to about 1200 milligrams of alpha lipoic acid, from about 400 milligrams to about 1200 milligrams of magnesium, and from about 75 milligrams to about 500 milligrams of gymnemic acid.

8. A composition according to claim 1, further comprising a pharmaceutically acceptable carrier.

9. In a method for modulating nutrient partitioning in a human so as to increase oxidation of fat and increase storage of glycogen, comprising orally or parenterally administering to a human for a therapeutically effective period an effective amount of a composition comprising
    an effective amount of hydroxycitric acid;
    an effective amount of carnitine;
    an effective amount of biotin; and
    an effective amount of one or more gluconeogenic substrates selected from the group consisting of aspartate, lactate, glycerol, and a gluconeogenic amino acid or alphaketo analogue thereof;
    the improvement comprising the addition of an effective amount of eicosapentanoic acid.

10. A method according to claim 9, wherein the composition is administered on a daily basis to said human.

11. A method according to claim 10, wherein said therapeutically effective period of time is at least three weeks.

12. A method according to claim 10, wherein the effective amount of the composition is at least about 1 gram per serving.

13. A method according to claim 10, wherein the effective amount of the composition is from about 4 gram to about 20 grams per serving.

14. A method according to claim 9, wherein the composition comprises: a weight ratio of the hydroxycitric acid to the carnitine of from about 1:10 to about 100:1; a weight ratio of the hydroxycitric acid to the gluconeogenic substrate of from about 5:1 to about 1:60; and a weight ratio of the hydroxycitric acid to the biotin of from about 50:1 to about 2500:1.

15. A method according to claim 9, wherein the gluconeogenic amino acid is selected from the group consisting of: alanine, arginine, asparagine, cystine, glutamine, glycine, histidine, hydroxyproline, methionine, proline, serine, threonine, and valine.

16. A method according to claim 9, wherein the composition further comprises an effective amount of at least one nutritional supplement.

17. A method according to claim 16, wherein the nutritional supplement is selected from the group consisting of: chromium, conjugated linoleic acid, coenzyme Q10, eicosapentaenoic acid, pyridoxine, alpha-lipoic acid, magnesium, and gymnema sylvestre.

18. A method according to claim 17, wherein the composition comprises: from about 0.2 grams to about 8 grams of hydroxycitric acid, from about 10 milligrams to about 10 grams of carnitine, from about 1 gram to about 75 grams of the gluconeogenic substrate; from about 1 milligram to about 25 milligrams of biotin, from about 100 micrograms to about 2 milligrams of chromium, from about 5 milligrams to about 500 milligrams of coenzyme Q10, from about 50 milligrams to about 20 grams of conjugated linoleic acid, from about 10 milligrams to about 10 grams of eicosapentaenoic acid, from about 25 milligrams to about 400 milligrams of pyridoxine, from about 25 milligrams to about 2000 milligrams of alpha lipoic acid, from about 200 milligrams to about 1600 milligrams of magnesium, and from about 20 milligrams to about 2000 milligrams of gymnemic acid.

19. A method according to claim 17, wherein the composition comprises: from about 0.5 grams to about 5 grams of hydroxycitric acid, from about 50 milligrams to about 5 grams of carnitine, from about 1 gram to about 30 grams of the gluconeogenic substrate; from about 2 milligrams to about 10 milligrams of biotin, from about 400 micrograms to about 1000 micrograms of chromium, from about 20 milligrams to about 300 milligrams of coenzyme Q10, from about 1 gram to about 10 grams of conjugated linoleic acid, from about 50 milligrams to about 5000 milligrams of eicosapentaenoic acid, from about 100 milligrams to about 300 milligrams of pyridoxine, from about 50 milligrams to about 1200 milligrams of alpha lipoic acid, from about 400 milligrams to about 1200 milligrams of magnesium, and from about 75 milligrams to about 500 milligrams of gymnemic acid.

20. A method according to claim 9, wherein the composition further comprises a pharmaceutically acceptable carrier.

21. A method according to claim 9, further including having said human follow a dietary regimen involving a glycemic index of less than 60 and daily calorie consumption comprising less than 50% of calories from carbohydrate intake and at least 20% of calories from protein intake.

22. A method according to claim 9, wherein the method further includes having said human follow an exercise program involving aerobic and resistance training.

23. A method according to claim 9, wherein the method further involves having the human donate blood so as to produce a fall in serum ferritin levels and iron stores.

24. A method according to claim 9, wherein the method further involves having the human follow a stress reduction program so as to diminish glycocorticoid activity.

* * * * *